United States Patent [19]

Okawa et al.

[11] Patent Number: 4,976,679

[45] Date of Patent: Dec. 11, 1990

[54] PROCESS FOR PRODUCING A URETHANE AND A CARBONIC ACID ESTER

[76] Inventors: Takashi Okawa; Nobuo Isogai; Tomoji Tsuji, all of 182, Aza Shinwari, Tayuuhama, Niigata-shi, Japan

[21] Appl. No.: 267,155

[22] Filed: Nov. 3, 1988

[30] Foreign Application Priority Data

Nov. 5, 1987 [JP] Japan ............................ 62-278328
Apr. 1, 1988 [JP] Japan ............................ 63-78000

[51] Int. Cl.$^5$ ............................................ C07C 125/06
[52] U.S. Cl. ................................. 560/159; 546/171; 546/309; 548/163; 548/557
[58] Field of Search ............... 560/115, 24, 25, 157, 560/114, 12, 22, 27, 28, 32, 33, 132–134, 157–158, 159, 166; 558/276, 277, 270, 275, 260, 274; 549/469, 480, 69; 546/171, 309; 548/163, 557; 552/514

[56] References Cited

U.S. PATENT DOCUMENTS

| | | | |
|---|---|---|---|
| Re. 29,338 | 8/1977 | Perratti et al. | 558/277 X |
| 4,426,331 | 1/1984 | Drent | 558/277 |
| 4,625,044 | 11/1986 | Curnutt | 558/277 |
| 4,785,130 | 11/1988 | Bhattacharya | 558/277 |

FOREIGN PATENT DOCUMENTS

| | | |
|---|---|---|
| 1150292 | 7/1983 | Canada . |
| 0173457 | 3/1986 | European Pat. Off. . |
| 2603574 | 5/1979 | Fed. Rep. of Germany . |
| 57-32251 | 2/1982 | Japan . |
| 57-32250 | 3/1982 | Japan . |
| 59-172451 | 9/1984 | Japan . |
| 1080094 | 8/1967 | United Kingdom . |
| 1402379 | 8/1975 | United Kingdom . |

*Primary Examiner*—Werren B. Lone
*Attorney, Agent, or Firm*—Lorraine M. Donaldson

[57] ABSTRACT

The present invention relates to a process for producing a urethane and a carbonic acid ester which comprises reacting a primary amine, an organic compound containing a hydroxyl group(s), carbon monoxide and molecular oxygen with one another by using a catalyst comprising mainly copper.

7 Claims, 1 Drawing Sheet

PROCESS FOR PRODUCING A URETHANE AND A CARBONIC ACID ESTER

BACKGROUND OF THE INVENTION

1. Field of the Invention

The present invention relates to a process for producing a urethane and a carbonic acid ester which comprises reacting a primary amine, an organic compound containing a hydroxyl group(s), carbon monoxide and molecular oxygen with one another by using a catalyst comprising mainly copper.

Urethanes are per se important compounds as substrate for carbamate based agricultural chemicals, and since they can easily be converted into isocyanates for producing polyurethanes, by heat treatment, there has recently been desired a process for producing them at low cost as intermediates for producing isocyanates without using phosgene which is poisonous.

On the other hand, carbonic acid esters are useful not only as starting materials for producing polycarbonates, but also as esterifying agents, solvents, etc.

2. Description of the Prior Art

Urethanes and carbonic acid esters have heretofore been produced by reacting phosgene with primary amines or alcohols, but in recent years, there have proposed various methods using no phosgene which is very poisonous.

The methods for producing urethanes without using phosgene are roughly divided into two groups, namely, methods of using nitro compounds as starting materials and methods of using primary amines as starting materials.

The methods using nitro compounds as starting materials comprise reacting a nitro compound such as nitrobenzene, an organic compound containing a hydroxyl group(s), such as an alcohol, and carbon monooxide with one another in the presence of a catalyst comprising mainly a compound of an element of the platinum group, e.g., palladium or rhodium, or selenium, and thereby producing a urethane reductively, and they are disclosed, for example, in British Patent Nos. 1080094 and 1402379. Japanese Patent Kokai (Laid-Open) Nos. 57-32250 and 57-32251 disclose methods for producing a urethane and a carbonic acid ester at the same time by reacting an aromatic nitro compound, an organic compound containing a hydroxyl group(s), and carbon monoxide with one another in the presence of a catalyst comprising mainly palladium.

On the other hand, the methods using primary amines as starting materials comprise using molecular oxygen or a nitro compound as an oxidizing agent, reacting a primary amine such as aniline, an organic compound containing a hydroxyl group(s), and carbon monoxide with one another in the presence of a catalyst comprising mainly a compound of an element of the platinum group, e.g., palladium, rhodium or ruthenium, and thereby producing a urethane oxidatively. These oxidative carbonylation methods are disclosed, for example, in Canadian Patent No. 1150292, U.S. Pat. Nos. 4490551, 4297501 and 4547322.

In the methods using a nitro compound or a primary amine as a starting material, a catalyst comprising a compound of an element of the platinum group or selenium is used, but since the main catalyst itself has only low urethane synthesizing activity, there have been developed catalytic systems consisting of combinations of the main catalyst and co-catalysts such as iron chloride, iron oxychloride, vanadium oxychloride, lithium hydroxide, halides and Lewis acids, or ligands such as pyridine and quinoline. Employment of these co-catalysts or ligands, however, is disadvantageous in that although the urethane synthesizing activity is improved, a complicated catalyst composed of many components is used, so that a troublesome procedure and a great cost are required for recovering, for reuse, the expensive compound of the element of the platinum group efficiently from the reaction mixture after the reaction.

SUMMARY OF THE INVENTION

The present inventors conducted various research on catalysts for producing a urethane by reacting a primary amine, carbon monoxide, molecular oxygen, and an organic compound containing a hydroxyl group(s), with one another, and consequently found that a urethane and a carbonic acid ester can be efficiently produced by carrying out the above reaction in the presence of a catalyst containing copper and a halogen(s) as active ingredients which is utterly different from conventional catalytic systems, and that particularly in production of an aliphatic urethane, the urethane yield can be greatly improved by carrying out the above reaction in the presence of an oxygen-containing organic sulfur compound together with the catalyst comprising mainly copper, whereby the present invention has been accomplished.

That is, the first aspect of the invention is a process for producing a urethane and a carbonic acid ester which comprises reacting a primary amine, carbon monoxide, molecular oxygen, and an organic compound containing a hydroxyl group(s), with one another by using a catalytic system comprising at least one member selected from the group consisting essentially of copper and copper-containing compounds and at least one halogen selected from the group consisting of iodine, chlorine and bromine.

The second aspect of the invention is a process for producing a urethane and a carbonic acid ester which comprises reacting a primary amine, an organic compound containing a hydroxyl group(s), carbon monoxide and molecular oxygen with one another in the presence of a catalytic system containing copper and a halogen(s) as active ingredients by making coexist an oxygen-containing organic sulfur compound of 1 mole or more per mole of the amino group of the primary amine. In the case of the second aspect of the invention, high yields can be attained particularly when an aliphatic primary amine is used as a starting material.

The present invention is markedly characterized in that it uses a novel catalytic system comprising mainly copper which is utterly different from conventional catalytic systems comprising mainly an element of the platinum group or selenium, and in that in the presence of an organic hydroxy compound, a high urethane-synthesizing activity can be attained in oxidative carbonylation reaction of a primary amine.

DETAILED DESCRIPTION OF THE INVENTION

Figure 1:
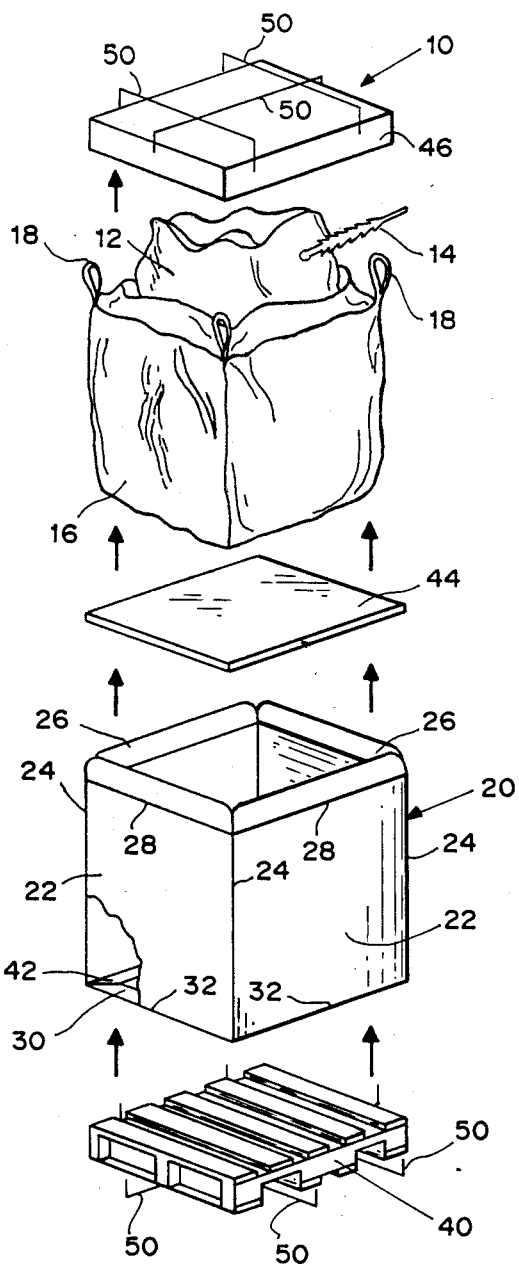

In the process of the present invention, one and the same catalytic system permits production of a urethane and a carbonic acid ester, and therefore we conjecture that two reactions represented by the following general formulas proceed at the same time:

$$R_1(NH_2)_n + n \cdot CO + \tfrac{1}{2}n \cdot O_2 + n \cdot R_2OH \rightarrow R_1(NH\text{-}COOR_2)_n + n \cdot H_2O \quad (1)$$

$$2R_2OH + CO + \tfrac{1}{2}O_2 \rightarrow CO(OR_2)_2 + H_2O \quad (2)$$

wherein each of $R_1$ and $R_2$ is an alkyl group or an aryl group, and n is an integer of 1 or more.

As the copper catalyst used in the process of the present invention, any catalyst may be used so long as it contains copper as a component, and either metallic copper or a component constituting a copper compound may be used. The copper catalyst may be supported on a carrier, for example, active carbon, graphite, silica, or alumina. Copper compounds usable as the catalyst include, for example, inorganic compounds such as copper iodide, copper bromide, copper chloride, copper oxide, copper sulfate, copper nitrate, and the like; copper salts of organic acids, such as copper acetate, copper oxalate, copper formate, and the like; and copper salts or copper complex compounds which contain ammonia, amines, phosphine, carbon monoxide, chelate ligands, etc.

The amount of the copper catalyst used is 0.001 to 100 gram atoms, preferably 0.01 to 10 gram atoms in terms of copper atom per mole of the amino group of the primary amine. When the amount is less than 0.001 gram atom, the reaction rate is too slow. When the amount exceeds 100 gram atoms, no adverse effect is brought about but such an amount is not economical. Therefore, the above range is practical.

The halogen used in the present invention is selected from iodine, bromine and chlorine. These halogens may be used alone or as a mixture of two or more. Among them, iodine is particularly preferred. The halogen may be used in the form of either halogen molecule itself or an organic or inorganic halogen-containing compound. The halide includes, for example, halides of metals such as alkali metals, alkaline earth metals, etc.; halogenated onium compounds, e.g., ammonium salts and phosphonium salts; oxoacids of halogens or salts thereof; and organic halides, e.g., methyl halides and ethyl halides.

The amount of the halogen used is 0.01 to 100 gram atoms, preferably 0.1 to 10 gram atoms in terms of halogen atom per gram atom of copper.

Although the catalyst of the present invention contains mainly copper and the halogen as active ingredients, there can be properly used in combination therewith other elements, for example, tellurium, sulfur, antimony, bismuth, zinc, tin, vanadium, iron, cobalt, nickel, manganese, thallium, chromium, molybdenum, and tungsten.

The oxygen-containing organic sulfur compound used in the second aspect of the invention includes sulfones and sulfoxides. Specific examples of the oxygen-containing organic sulfur compound include dimethyl sulfone, sulfolane, 2-methyl sulfolane, diphenyl sulfone, dimethyl sulfoxide, diethyl sulfoxide, tetramethyl sulfoxide, and diphenyl sulfoxide. Among them, sulfolane is particularly preferred.

The amount of the oxygen-containing organic sulfur compound used is 1 mole or more, preferably 2 to 20 moles per mole of the amino group of the primary amine. When the amount is less than 1 mole, the addition of said compound has only insufficient effect. When the amount is more than 20 moles, the space time yield is lowered. Therefore, the above range is practical.

The primary amine as starting material in the present invention includes aliphatic, aromatic, alicyclic and heterocyclic compounds having in the molecule at least one amine group.

The aromatic or heterocyclic amines include, for example, aniline, 1,2-diaminobenzene, 1,4-diaminobenzene, isomers of chloroaniline, 3,4-dichloroaniline, 4-isopropylaniline, p-toluidine, chlorotoluidine, xylidine, alkoxyanilines, isomers of nitroaniline, 2,3-diaminotoluene, 2,4-diaminotoluene, 2,6-diaminotoluene, 2,5-diaminotoluene, 3,4-diaminotoluene, 3,5-diaminotoluene, 2-amino-4-nitrotoluene, 2-amino-3-nitrotoluene, 2-amino-5-nitrotoluene, aminophenols, diaminoxylene, aminonitroxylenes, aminonaphthalenes, amino-anthracenes, chloroaminobenzoic acids, aminobenzenesulfonic acids, 4,4-diaminodiphenylmethane, 2,2-diaminodiphenylmethane, 2,4-diaminodiphenylmethane, tris(4-aminophenyl)methane, aminopyridines, aminoquinolines, aminopyrroles, aminofurans, aminothiophenes, and 2-aminobenzothiazoles.

The alicyclic amines include, for example, aminocyclobutane, aminocyclopentane, cyclohexylamine, 1,2-diaminocyclohexane, 1,3-diaminocyclohexane, 1,4-diaminocyclohexane, and bis(aminocyclohexyl)methanes.

The aliphatic amines include, for example, methyl amine, ethylamine, 1-propylamine, 2-propylamine, 1-butylamine, 2-butylamine, isobutylamine, t-butylamine, 1-pentylamine, 1-hexylamine, 1-heptylamine, 1-octylamine, 1-decylamine, 1-dodecylamine, ethylenediamine, diaminopropanes, diaminobutanes, diaminopentanes, diaminohexanes such as 1,6-hexamethylenediamine, etc., diaminooctanes, diaminodecanes, benzylamine, bis(aminomethyl)cyclohexanes, and bis(aminomethyl)benzenes such as m-xylenediamine, etc.

The organic compound containing a hydroxyl group(s) used in the present invention includes alcohols and phenols which have at least one OH group in the molecules.

The alcohols include, for example, methanol, ethanol, n-propanol, isopropanol, n-butanol, t-butanol, n-pentanol, n-hexanol, cyclohexanol, benzyl alcohol, cycloethanol, ethylene glycol, diethylene glycol, propylene glycol, glycerol, and trimethylolpropane.

The phenols include, for example, phenol, naphthols, anthranol, phenanthrol, and hydroxybenzofurans.

The amount of these organic compounds containing a hydroxyl group(s) used is 1 mole or more, preferably 5 moles or more per mole of the amino group of the primary amine. Although not critical, the upper limit of the amount is 200 moles or less in practice. When the amount exceeds 200 moles, the space time yield is lowered. Therefore, it is not desirable.

Although the process of the present invention does not particularly require a solvent, solvents inert toward the reaction can be used in said process. The solvents include, for example, aliphatic hydrocarbons such as pentane, hexane, heptane, octane, and the like; alicyclic hydrocarbons such as cyclohexane, tetralin, and the like; aromatic hydrocarbons such as benzene, toluene, xylene, and the like; nitriles such as acetonitrile, benzonitrile, and the like; ethers such as tetrahydrofuran, 1,4-dioxane, and the like; ketones such as acetone, methyl ethyl ketone, and the like; esters such as ethyl acetate, ethyl benzoate, and the like; and halogenated hydrocarbons such as chlorobenzene, dichlorobenzene, chlorohexane, trichlorotrifluoroethane, and the like.

As the molecular oxygen used in the present invention, pure oxygen and air can be used as they are or after being diluted with other gases which do not inhibit the reaction, for example, inert gases such as argon, helium, nitrogen, carbon dioxide, etc.

As the carbon monoxide used in the present invention, there can be used pure carbon monoxide, and mixed gases of carbon monoxide, the above-mentioned inert gases and if necessary, hydrogen, hydrocarbon gases, etc.

The reaction temperature in the present invention is 50° to 300° C., preferably 100° to 250° C. When it is lower than 50° C., the reaction rate is decreased. When it is higher than 300° C., side reactions are promoted.

The reaction pressure is 1 to 500 kg/cm$^2$G, and in practice, it is preferably 20 to 300 kg/cm$^2$G. Although varied depending on catalytic system, the amount of catalyst, reaction conditions, etc., the reaction time is usually several minutes to several hours.

The present invention can be suitably conducted either in a batchwise manner or continuously. The reaction mixture in the present invention is first freed from the catalyst by filtration and then heated and evaporated to be concentrated or dried up, after which the urethane precipitated was separated by filtration or solvent extraction. The distillate obtained by the evaporation is separated into the compound containing a hydroxyl group(s) (an alcohol), a carbonic acid ester, the unreacted amine, and low-boiling by-products, followed by recovery.

EFFECT OF THE INVENTION

The present invention is a process for producing a urethane and a carbonic acid ester from a primary amine, an organic compound containing a hydroxyl group(s), carbon monoxide and molecular oxygen, and is advantageous in that unlike conventional processes, it neither requires handling of phosgene which is highly poisonous, nor yields hydrochloric acid as a by-product.

Conventional catalytic systems comprise mainly expensive elements of the platinum group, such as palladium, rhodium and ruthenium, or selenium which is poisonous, and they are disadvantageous in that there is no choice but to use co-catalysts containing foreign metallic elements, ligands, additives, etc. in a large amount in order to secure the activity and stability of catalyst, so that the catalytic systems tend to be composed of many components and to become complicated.

On the other hand, the process of the present invention is advantageous in that a high activity can be attained by means of a catalytic system comprising mainly copper which is not expensive, and that since the catalyst is a simple system and does not contain any foreign metal, the catalyst can be smoothly recovered and reused.

Thus, according to the process of the present invention, by the oxidative carbonylation reaction of an aromatic or aliphatic primary amine in the presence of an organic compound containing a hydroxyl group(s), corresponding urethanes and carbonic ester can be efficiently produced. Therefore, said process is industrially advantageous.

The process of the second aspect of the invention is advantageously used particularly for producing an aliphatic urethane which can be used as a material for hexamethylene diisocyanate and m-xylene diisocyanate.

EXAMPLES

The process of the present invention is more concretely illustrated with the following examples.

Example 1

An autoclave made Hastelloy having a capacity of 100 ml was charged with 1 g (10.7 m moles) of aniline, 25 g (543 m moles) of ethanol and 0.48 g (2.52 m moles) of copper iodide, and hermetically sealed. Carbon monoxide, and air were put in the autoclave to adjust their partial pressures to 75 kg/cm$^2$G and 35 kg/cm$^2$G, respectively, and the reaction was carried out at a temperature of 158° C. for 2 hours.

After completion of the reaction, the residual gas was purged while cooling the autoclave, and the reaction mixture was analyzed by an internal standard method by a high performance liquid chromatography and a gas chromatography.

Consequently, the urethane (ethyl N-phenyl-carbamate) yield based on aniline was 92.3%, and 0.91 m moles of diethyl carbonate was found to be produced at the same time.

Examples 2 to 5

Reaction was carried out in the same manner as in Example 1, except that the reaction temperature was changed to 175° C., 165° C., 145° C. or 132° C. The urethane yield based on aniline and the amount of diethyl carbonate obtained are shown in Table 1.

TABLE 1

| Example No. | Reaction temp. (°C.) | Urethane yield mol % | Amount of diethyl carbonate obtained m mol |
|---|---|---|---|
| 2 | 175 | 50.4 | 2.10 |
| 3 | 165 | 86.5 | 4.38 |
| 4 | 145 | 82.3 | 0.77 |
| 5 | 132 | 68.6 | — |

Example 6

Reaction was carried out in the same manner as in Example 1, except for using 0.16 g (2.52 m moles) of metallic copper and 0.38 g (2.52 m moles) of sodium iodide as catalysts.

Consequently, the urethane yield based on aniline was 42.2% and the amount of diethyl carbonate obtained was 7.05 m moles.

Example 7

The same autoclave as in Example 1 was charged with 1 g (8.61 m moles) of 1,6-hexamethylenediamine, 25 g (780 m moles) of methanol and 0.48 g (2.52 m moles) of copper iodide in the same manner as in Example 1. Carbon monoxide and air were put in the autoclave to adjust their partial pressures to 75 kg/cm$^2$G and 35 kg/cm$^2$G, respectively, and the reaction was carried out at a temperature of 175° C. for 1 hour.

Consequently, the diurethane (dimethyl 1,6-hexamethylenecarbamate) yield based on 1,6-hexamethylenediamine was 66.6% and 4.45 m moles of dimethyl carbonate was produced at the same time.

Example 8

Reaction was carried out in the same manner as in Example 7, except for using 1 g (7.34 m moles) of m- xylenediamine as a starting material. Consequently, the diurethane [dimethyl 1,3-phenylenebis(methylene)biscarbamate] yield based on m-xylenediamine (hereinafter referred as MXDA) was 66.8% and the amount of dimethyl carbonate obtained was 7.53 m moles.

Example 9

Reaction was carried out in the same manner as in Example 8, except for using 0.25 g (2.52 m moles) of copper chloride as a catalyst. Consequently, the diurethane yield based on MXDA was 37.9% and 7.11 m moles of dimethyl carbonate was produced at the same time.

Example 10

An autoclave made of Hastelloy having a capacity of 100 ml was charged with 1 g (7.34 m moles) of MXDA, 8 g (250 m moles) of methanol, 6 g (49.9 m moles) of sulfolane and 0.48 g (2.52 m moles) of copper iodide, and hermetically sealed. Carbon monoxide and air were put in the autoclave to adjust their partial pressures to 75 kg/cm$^2$G and 35 kg/cm$^2$G, respectively, and the reaction was carried out at a temperature of 165° C. for 2 hours.

After completion of the reaction, the residual gas was purged while cooling the autoclave, and the reaction mixture was analyzed by an internal standard method by a high performance liquid chromatography and a gas chromatography.

Consequently, the diurethane [dimethyl 1,3-phenylenebis(methylene)biscarbamate] yield based on MXDA was 91.9%, and 1.86 m moles of dimethyl carbonate was found to be produced at the same time.

Example 11 and 12

Reaction was carried out in the same manner as in Example 10, except that the molar ratio of sulfolane to the amino group was changed to 4.54 or 9.65.

The diurethane yield based on MXDA and the amount of dimethyl carbonate obtained are shown in Table 2.

TABLE 2

| Example No. | Sulfolane Amino Group mol/mol | Urethane yield mol % | Amount of dimethyl carbonate obtained m mol |
|---|---|---|---|
| 11 | 4.54 | 89.2 | 3.31 |
| 12 | 9.65 | 92.0 | 1.84 |

Example 13

Reaction was carried out in the same manner as in Example 10, except that 17 g (218 m moles) of dimethyl sulfoxide was used in place of sulfolane. Consequently, the diurethane yield based on MXDA was 85.5% and the amount of dimethyl carbonate obtained was 5.81 m moles.

Example 14

Reaction was carried out under the same conditions as in Example 1, except for using 8 g (174 m moles) of ethanol as an alcohol material. Consequently, the diurethane [diethyl 1,3-phenylenebis(methylene)biscarbamate] yield based on MXDA was 89.0% and the amount of diethyl carbonate obtained was 0.59 m moles.

Example 15

The same autoclave as in Example 10 was charged with 1 g (8.61 m moles) of 1,6-hexamethylenediamine as amine material, 8 g (250 m moles) of methanol, 6 g (49.9 m moles) of sulfolane and 0.48 g (2.52 m moles) of copper iodide. Carbon monoxide and air were put in the autoclave under pressure to adjust their partial pressures to 75 kg/cm$^2$G and 35 kg/cm$^2$G, respectively, and the reaction was carried out at a temperature of 175° C. for 1 hour. Consequently, the diurethane (dimethyl 1,6-hexamethylenecarbamate) yield based on 1,6-hexamethylenediamine was 82.3% and 3.21 m moles of dimethyl carbonate was produced at the same time.

Example 16

The same autoclave as in Example 10 was charged with 1 g (10.7 m moles) of aniline, 8 g (173.6 m moles) of ethanol, 8 g (66.6 m moles) of sulfolane and 0.48 g (2.52 m moles) of copper iodide. Carbon monoxide and air were put in the autoclave under pressure to adjust their partial pressures to 75 kg/cm$^2$G and 35 kg/cm$^2$G, respectively, and the reaction was carried out at a temperature of 158° C. for 2 hours. Consequently, the urethane (ethyl N-phenylcarbamate) yield based on aniline was 95.8% and the amount of diethyl carbonate obtained was 0.52 m moles.

Comparative Example 1

The same autoclave as in Example 1 was charged with 1 g (7.34 m moles) of MXDA and 8 g (250 m moles) of methanol as starting materials and 0.48 (2.52 m moles) of copper iodide, and they were reacted in the same manner as in Example 10 without sulfolane. Consequently, the diurethane yield based on MXDA was 60.9% and 2.47 m moles of dimethyl carbonate was produced at the same time.

Comparative Example 2

Reaction was carried out in the same manner as in Example 13, except that 17 g (151 m moles) of chlorobenzene was used in place of sulfolane. Consequently, the diurethane yield based on MXDA was 60.3% and the amount of dimethyl carbonate obtained was 1.43 m moles.

Comparative Example 3

Reaction was carried out in the same manner as in Example 10, except that the molar ratio of sulfolane to the amino group was changed to 0.85. Consequently, the diurethane yield based on MXDA was 64.8% and 4.76 m moles of dimethyl carbonate was produced at the same time.

What is claimed is:

1. A process for producing a urethane and a carbonic acid ester which comprises reacting a primary amine, carbon monoxide, molecular oxygen and an organic compound selected from the group consisting of phenols and aliphatic hydroxy compounds with one another by using a catalytic system consisting essentially of at least one member selected from the group consisting of copper and copper compounds and at least one halogen selected from the group consisting of iodine, chlorine and bromine.

2. A process for producing a urethane and a carbonic acid ester according to claim 1, wherein a catalyst consisting essentially of at least one member selected from the group consisting of copper and copper compounds and iodine are used.

3. A process for producing a urethane and a carbonic acid ester according to claim 1, wherein the reaction is carried out at a temperature of 50° to 300° C. and under a pressure of 1 to 500 kg/cm$^2$G.

4. A process for producing a urethane and a carbonic acid ester according to claim 1, wherein the reaction is carried out at a temperature of 100° to 250° C. and under a pressure of 20 to 300 kg/cm$^2$G.

5. A process for producing a urethane and a carbonic acid ester which comprises reacting a primary amine, carbon monoxide, molecular oxygen and an organic compound selected from the group consisting of phenols and aliphatic hydroxy compounds with one another in the presence of a catalytic system consisting essentially of copper and a halogen as active ingredients, and in the presence of an oxygen-containing organic sulphur compound selected from the group consisting of sulfones and sulfoxides of 1 mole or more per mole of the amino group of the primary amine.

6. A process for producing a urethane and a carbonic acid ester according to claim 5, wherein the primary amine is aliphatic.

7. A process for producing a urethane and a carbonic acid ester according to claim 5, wherein the oxygen-containing organic sulfur compound is sulfolane.

* * * * *

UNITED STATES PATENT AND TRADEMARK OFFICE
CERTIFICATE OF CORRECTION

Figure 2:
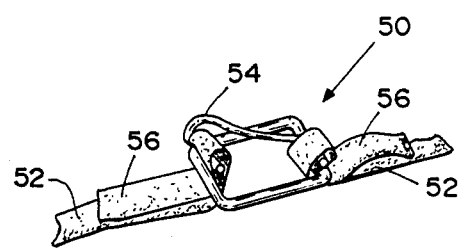
Figure 3:
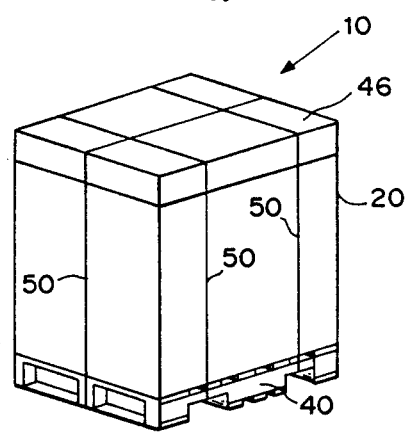

PATENT NO. : 4,976,679
DATED : December 11, 1990
INVENTOR(S) : Takashi OKAWA et al It is certified that error appears in the above-identified patent and that said Letters Patent is hereby corrected as shown below:

On the cover page, insert after Item [76],

-- [73] Assignee: Mitsubishi Gas Chemical Company, Inc. --;

On the cover page, delete the drawing;

On the drawing sheet, delete Figures 1-3.

Signed and Sealed this

Sixth Day of April, 1993

Attest:

STEPHEN G. KUNIN

Attesting Officer

Acting Commissioner of Patents and Trademarks